(12) United States Patent
Lee et al.

(10) Patent No.: US 8,653,297 B2
(45) Date of Patent: Feb. 18, 2014

(54) SOLID ACID, POLYMER ELECTROLYTE MEMBRANE INCLUDING THE SAME, AND FUEL CELL USING THE POLYMER ELECTROLYTE MEMBRANE

(75) Inventors: Jae-jun Lee, Yongin-si (KR); Myung-sup Jung, Yongin-si (KR); Do-yun Kim, Yongin-si (KR); Jin-gyu Lee, Yongin-si (KR); Sang-kook Mah, Yongin-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 313 days.

(21) Appl. No.: 13/238,885

(22) Filed: Sep. 21, 2011

(65) Prior Publication Data

US 2012/0045711 A1  Feb. 23, 2012

Related U.S. Application Data

(62) Division of application No. 11/580,733, filed on Oct. 12, 2006, now Pat. No. 8,049,032.

(30) Foreign Application Priority Data

Oct. 12, 2005 (KR) .......................... 10-2005-0096243

(51) Int. Cl.
*C07C 309/00* (2006.01)
*H01M 8/10* (2006.01)

(52) U.S. Cl.
USPC ............................................. 562/42; 429/494

(58) Field of Classification Search
USPC .............................................. 562/42; 429/494
See application file for complete search history.

(56) References Cited

U.S. PATENT DOCUMENTS

| | | | |
|---|---|---|---|
| 5,409,959 | A | 4/1995 | Hwang et al. |
| 7,052,793 | B2 | 5/2006 | Formato et al. |
| 7,345,135 | B2 | 3/2008 | Ishikawa et al. |
| 7,465,780 | B2 | 12/2008 | Jung et al. |
| 2002/0045085 | A1 | 4/2002 | Formato et al. |
| 2003/0187081 | A1 | 10/2003 | Cui |
| 2005/0118479 | A1 | 6/2005 | Yamaguchi et al. |
| 2005/0271921 | A1 | 12/2005 | Kim et al. |
| 2006/0127727 | A1 | 6/2006 | Lee et al. |

FOREIGN PATENT DOCUMENTS

| | | | |
|---|---|---|---|
| CN | 1406150 | A | 3/2003 |
| CN | 1707832 | A | 12/2005 |
| CN | 1786047 | A | 6/2006 |
| JP | 60-203603 | | 10/1985 |
| JP | 63-072669 | | 4/1988 |
| JP | 04-157456 | | 5/1992 |
| JP | 6-505477 | T | 6/1994 |
| JP | 2003-162100 | | 6/2003 |
| JP | 2003-263998 | A | 9/2003 |
| JP | 2004-010677 | | 1/2004 |
| JP | 2004-279838 | | 10/2004 |
| JP | 2005-087962 | | 4/2005 |
| JP | 2005-105176 | | 4/2005 |
| JP | 2005-232456 | A | 9/2005 |
| JP | 2005-285549 | | 10/2005 |
| KR | 10-2005-0024812 | A | 3/2005 |
| WO | WO 2005/050671 | A2 | 6/2005 |

OTHER PUBLICATIONS

Maksimov, A. L. et al., "*Supramolecular Catalysts on the Basis of Molecules-Receptors*", Ind. Eng. Chem. Res., 2005, vol. 44, pp. 8644-8653.
Nishikubo, T. et al., "*Synthesis and Photochemical Reaction of Cyclic Oligomers: Synthesis and Photopolymerization of Novel C-Methylcali[4]resorcinarene and p-Alkylcalix[n]arene Derivatives Containing Spiro Ortho Ether Groups*", Journal of Polymer Science: Part A: Polymer Chemistry, 2002, vol. 40, pp. 1293-1302.
SIPO Office action dated Jan. 29, 2010, for corresponding Chinese application 200610131779.6.
SIPO Office action dated Dec. 7, 2010, for corresponding Chinese application 20061013779.6, with English language translation.
SIPO Certificate of Patent dated Dec. 8, 2010, for Chinese application 200610162591.8.
Japanese Patent Office action dated Sep. 29, 2009, for Japanese application 2006-279041.
Japanese Patent Office action dated Oct. 19, 2010, for Japanese application 2007-044193.
U.S. Office action dated Aug. 5, 2010, for cross-reference U.S. Appl. No. 11/651,828.
U.S. Office action dated Dec. 22, 2010, for cross-reference U.S. Appl. No. 11/651,828.
U.S. Office action dated Apr. 5, 2011, for cross-reference U.S. Appl. No. 11/651,828.
SIPO Office action dated Jun. 4, 2013, with English translation, for corresponding Chince Patent application 201210138572.7, (15 pages).
Nishihara, M., et al., *Arginine magic with new counterions up the sleeve*, Organic & Biomolecular Chemistry, vol. 3, No. 9, Apr. 7, 2005, pp. 1659-1669.
Ludwig, R., et al., *Trivalent lanthanide and actinide extraction by calixarenes with different ring sizes and different molecular flexibility*, Radiochimica Acta, vol. 88, No. 6, Dec. 31, 2000, pp. 335-343.

(Continued)

*Primary Examiner* — Johann R Richter
*Assistant Examiner* — Kofi Adzamli
(74) *Attorney, Agent, or Firm* — Christie, Parker & Hale, LLP

(57) ABSTRACT

A solid acid having a core of calixarene or calix resorcinarene. The solid acid is an ion conducting compound in which at least one of the hydroxyl groups is substituted by an organic group having a cation exchange group at a terminal end, a polymer electrolyte membrane including the same, and a fuel cell using the polymer electrolyte membrane. The polymer electrolyte membrane can provide low methanol crossover and high ionic conductivity. Accordingly, a fuel cell having high efficiency can be obtained by using the polymer electrolyte membrane.

5 Claims, 8 Drawing Sheets

(56) References Cited

OTHER PUBLICATIONS

Ohto, K., et al., *Adsorption Behavior of Lead Ion on Calyx[4]Arene Tetracarboxylic Acid Impregnated Resin*, Separation Science and Technology, vol. 37, No. 8, Dec. 31, 2002, pp. 1943-1958.
KIPO Office action dated Sep. 28, 2006, for Korean priority Patent application 10-2005-0096243, with English translation, 5 pages.
English translation of Japanese Publication 63-72669, 15 pages.
English translation of Japanese Publication 04-157456, 22 pages.
SIPO Patent Certificate Serial No. 991416 issued on Jul. 4, 2012 for corresponding Chinese Application No. 200610131779.6 filed Oct. 12, 2006 with partial English translation (25 pages).
SIPO Office action dated Sep. 30, 2011, for corresponding Chinese Patent application 200610131779.6, with English translation, 6 pages.
Maksimov, A., et al. *Supramolecular calixarene-based catalytic systems in the Wacker-oxidation of higher alkenes*, Journal of Molecular CatalysisA: Chemical 217, (2004), pp. 59-67.
U.S. Office action dated Mar. 3, 2011, for U.S. Appl. No. 11/580,733, 13 pages.
U.S. Notice of Allowance dated Aug. 9, 2011, for U.S. Appl. No. 11/580,733.

SOLID ACID, POLYMER ELECTROLYTE MEMBRANE INCLUDING THE SAME, AND FUEL CELL USING THE POLYMER ELECTROLYTE MEMBRANE

CROSS-REFERENCE TO RELATED PATENT APPLICATION

This application is a divisional of application Ser. No. 11/580,733 filed Oct. 12, 2006, which claimed priority to and the benefit of Korean Patent Application No. 10-2005-0096243, filed on Oct. 12, 2005, in the Korean Intellectual Property Office, the contents of which are incorporated herein in its entirety by reference.

BACKGROUND OF THE INVENTION

1. Field of the Invention

The present invention relates to a solid acid and a full cell using the same, and more particularly, to a sulfonated ionic conducting cross-linked copolymer having low methanol crossover and high ionic conductivity, and a fuel cell including the same.

2. Description of the Related Art

A fuel cell is an electrochemical device which directly transforms the chemical energy of hydrogen and oxygen which are contained in hydrocarbon materials such as methanol, ethanol, and natural gas into electric energy. The energy transformation process of a fuel cell is very efficient and environmentally-friendly.

Fuel cells can be classified into Phosphoric Acid Fuel Cells (PAFC), Molten Carbonate Fuel Cells (MCFC), Solid Oxide Full Cells (SOFC), Polymer Electrolyte Membrane Fuel Cells (PEMFC), and Alkaline Fuel Cells (AFC) according to the type of electrolyte used. All fuel cells operate on the same principle, but the type of fuel used, operating speed, the catalyst used and the electrolyte used are different. In particular, a PEMFC is capable of being used in small-sized stationary power generation equipment or a transportation system due to its high reaction speed, low operating temperature, high output density, rapid start-up, and sensitive response to output request variation.

The core part of a PEMFC is a Membrane and Electrode Assembly (MEA). An MEA generally includes a polymer electrolyte and 2 electrodes formed of a cathode and an anode, each of which is attached to the each side of the polymer electrolyte membrane. The polymer electrolyte membrane acts as a separator blocking direct contact between an oxidizing agent and a reducing agent, and electrically insulates the two electrodes while conducting protons. Accordingly, a good polymer electrolyte membrane has high proton conductivity, good electrical insulation, low reactant permeability, excellent thermal, chemical and mechanical stability under normal fuel cell conditions, and a reasonable price.

In order to meet these requirements, various types of polymer electrolyte membranes have been developed, and, in particular, a highly fluorinated polysulfonic acid membrane such as a NAFION™ membrane is a standard due to excellent durability and performance.

Moreover, in a Direct Methanol Fuel Cell (DMFC), an aqueous methanol solution is supplied as a fuel to the anode and a portion of non-reactive aqueous methanol solution is permeated to the polymer electrolyte membrane. The methanol solution that permeates to the polymer electrolyte membrane causes a swelling phenomenon in an electrolyte membrane, which makes the methanol solution diffuse to a cathode catalyst layer. Such a phenomenon is referred to as 'methanol crossover.' In this phenomenon, the direct oxidization of methanol occurs at the cathode where, otherwise, only electrochemical reduction of hydrogen ions and oxygen should occur. Therefore, electric potential can be degraded, thereby causing a significant decline in the performance of the fuel cell.

This issue is common in other fuel cells using a liquid fuel such as a polar organic fuel.

Since conventional polymer electrolyte membranes do not have both excellent ionic conductivity and low methanol crossover, improvements in polymer electrolyte membranes are required.

SUMMARY OF THE INVENTION

One embodiment of the present invention provides a solid acid which provides ionic conductivity to a polymer electrolyte membrane and is not easily separated from the polymer electrolyte membrane.

Another embodiment of the present invention also provides a polymer electrolyte membrane having high ionic conductivity and low methanol crossover by including the solid acid.

Yet another embodiment of the present invention also provides a fuel cell having high efficiency by using the polymer electrolyte membrane.

According to an embodiment of the present invention, a solid acid is provided having the core of calixarene or calixresorcinarene, wherein the solid acid is an ion conducting compound in which at least one of the hydroxyl groups is substituted by an organic group having a cation exchange group at a terminal.

According to another embodiment of the present invention, a polymer electrolyte membrane is provided including a polymer matrix and the solid acid in the polymer matrix described above. The polymer matrix may include at least one material selected from the group consisting of sulfonated poly(ether ether ketone) (SPEEK), sulfonated poly(ether ether sulfone) (SPEES), sulfonated polyimide (SPI), polyimide, polybenzimidazole, polyether sulfone, and poly(ether ether ketone).

According to another embodiment of the present invention, a fuel cell is provided including: a cathode; an anode; and the polymer electrolyte membrane interposed between the cathode the anode described above.

BRIEF DESCRIPTION OF THE DRAWINGS

The above and other embodiments of the present invention will become more apparent by describing exemplary embodiments thereof with reference to the attached drawings in which.

DETAILED DESCRIPTION

A solid acid according to an embodiment of the present invention includes a core of calixarene or calixresorcinarene, and is an ion conducting compound in which at least one of the hydroxyl groups is substituted by an organic group having a cation exchange group at a terminal.

The calixarene is represented by Formula 1 and the calixresorcinarene is represented by Formula 2:

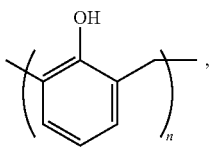

Formula 1 where n is an integer in the range of 4-6;

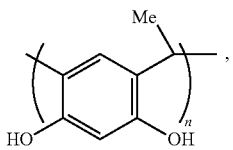

Formula 2 where n is an integer in the range of 4-6.

In an embodiment of the present invention, the calixresorcinarene of Formula 2 can be calix[4]resorcinarene represented by the formulas below:

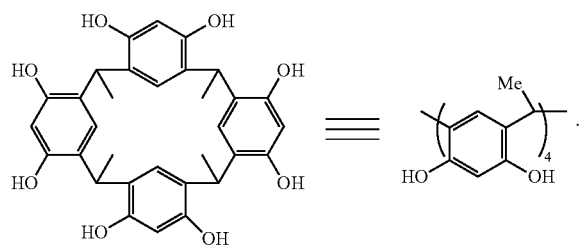

Figure 1A:
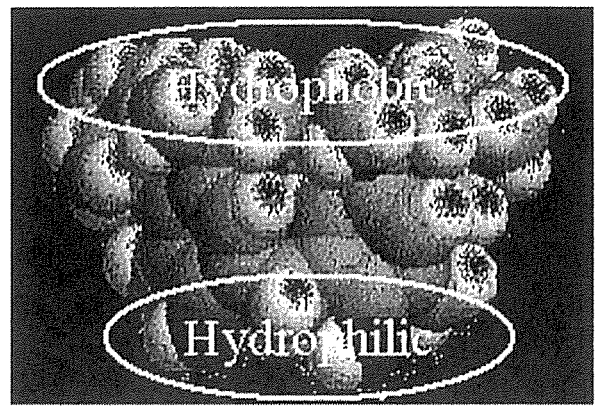
FIGS. 1A and 1B are three-dimensional views illustrating structures of calixarene and calixresorcinarene.
Figure 1B:
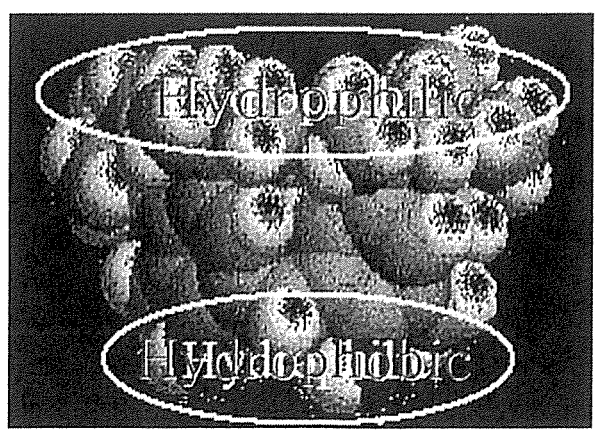

FIGS. 1A and 1B are three-dimensional views illustrating the structures of calixarene and calixresorcinarene.

Referring to 1A and 1B, since the cores of calixarene and calixresorcinarene are hydrophobic, water or alcohol barely contacts or permeates into the inner parts of the calixarene and calixresorcinarene. If such a structure is distributed in a polymer electrolyte membrane, the outward flow through the membrane is less. Also, since the calixarene and calixresorcinarene each have a large number of hydroxyl groups, the introduction of various sizes and types of substituents having a cation exchange group can be made according to a desired reaction.

If the solid acid of an embodiment is distributed in a polymer electrolyte membrane, the outward flow due to swelling barely occurs since the solid acid has a significantly large size. Also, the solid acid of one embodiment provides ionic conductivity to a polymer electrolyte membrane since the cation exchange group attached to the terminal such as —COOH, —$SO_3H$, and —$OPO(OH)_2$ provides high ionic conductivity.

Moreover, the solid acid of an embodiment can be dissolved or dispersed in an organic solvent, and the size and the number of acid groups as multi-acids in which a number of acid groups exist together can be controlled.

In the solid acid of one embodiment, an organic group having a cation exchange group at a terminal may be an unsubstituted or substituted $C_1$-$C_{20}$ alkoxy group having a cation exchange group at a terminal, an unsubstituted or substituted $C_6$-$C_{20}$ aryloxy group having a cation exchange group at a terminal, or an unsubstituted or substituted $C_2$-$C_{20}$ heteroaryloxy group having a cation exchange group at a terminal.

In an embodiment, the substituted or unsubstituted $C_1$-$C_{20}$ alkoxy group may be methoxy, ethoxy, propoxy, isobutyloxy, sec-butyloxy, pentyloxy, iso-amyloxy, hexyloxy whose alkyl is unsubstituted or substituted with a halogen atom, a hydroxyl group, a nitro group, a cyano group, an amino group, an amidino group, hydrazine, hydrazone, a carboxyl group or a salt thereof, a sulfonate group or a salt thereof, a phosphoric acid or a salt thereof, a $C_1$-$C_{20}$ alkyl group, an alkenyl group, a alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, or a $C_6$-$C_{20}$ heteroarylalkyl group.

In an embodiment, the $C_6$-$C_{20}$ aryloxy group is a carbon ring oxy group with a carbon number of 6-20 in which the carbon ring can be attached and fused using a pendent method. In one embodiment, the aryloxy group may be an aromatic system such as phenyloxy, naphthyloxy, tetrahydronaphthyloxy, or indanoxy. In another embodiment, the aryloxy group is phenyloxy or naphthyloxy. The aryloxy group can have substitutents such as alkyl halides, nitros, cyanos, alkoxys and lower alkyl aminos. Also, one or more hydrogen atoms among the aryloxy group can be substituted with a halogen atom, a hydroxyl group, a nitro group, a cyano group, an amino group, an amidino group, hydrazine, hydrazone, a carboxylic acid or salts thereof, a sulfonic acid or salts thereof, a phosphoric acid or salts thereof, a $C_1$-$C_{20}$ alkyl group, an alkenyl group, an alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, or a $C_6$-$C_{20}$ heteroarylalkyl group.

In one embodiment, the $C_2$-$C_{20}$ heteroaryloxy group includes one, two, or three hetero atoms selected from N, O, P or S, and is a monovalent monocyclic oxycompound or a bicyclic aromatic oxycompound in which the other cyclic atoms are C with a carbon number of 6-20. The heteroaryloxy group can be substituted with the same substituents as the alkoxy group described above.

In an embodiment, the organic group having a cation exchange group at the terminal can be represented by Formulas 3 through 6:

—O—$(CH_2)_kSO_3H$,  Formula 3 where k is an integer in the range of 1-5;

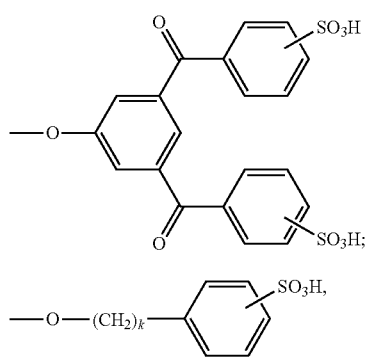
where k is an integer in the range of 1-5;
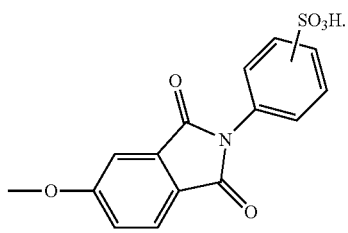
The solid acid of one embodiment is represented by one of Formulas 7-10.
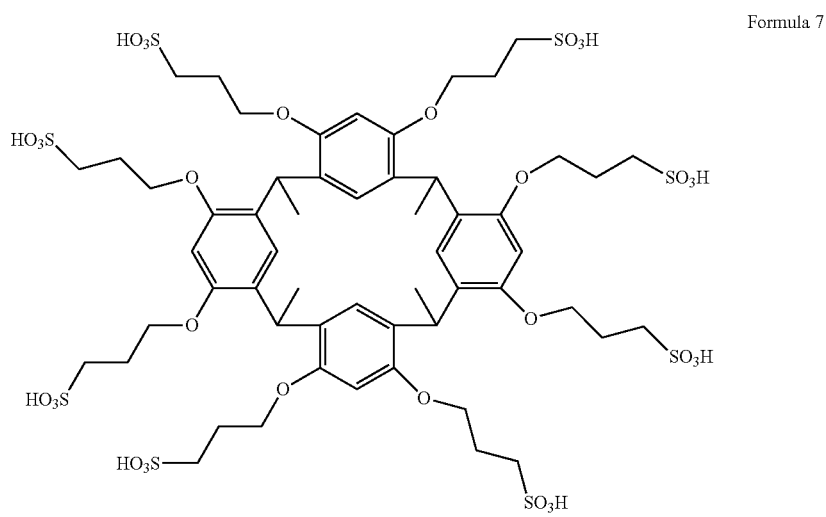
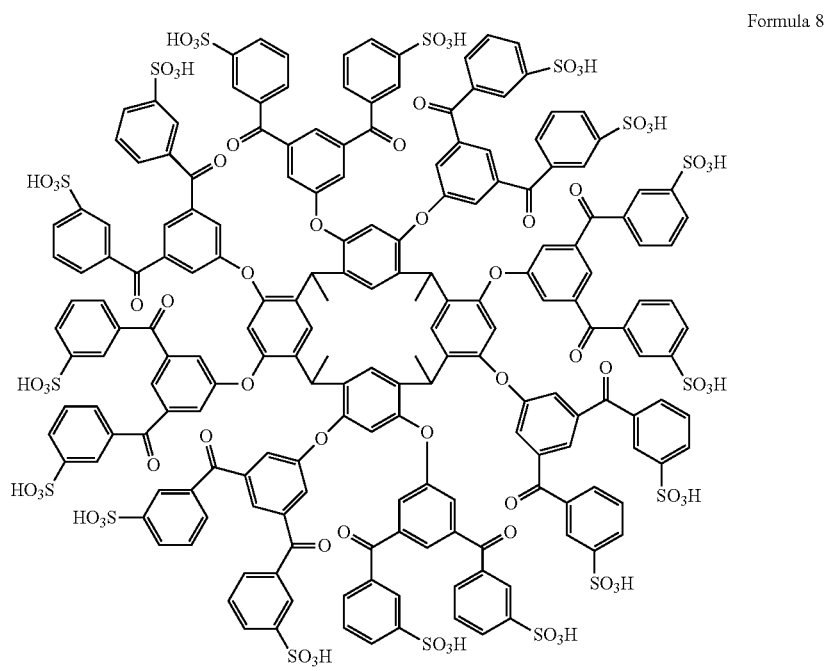

Formula 9
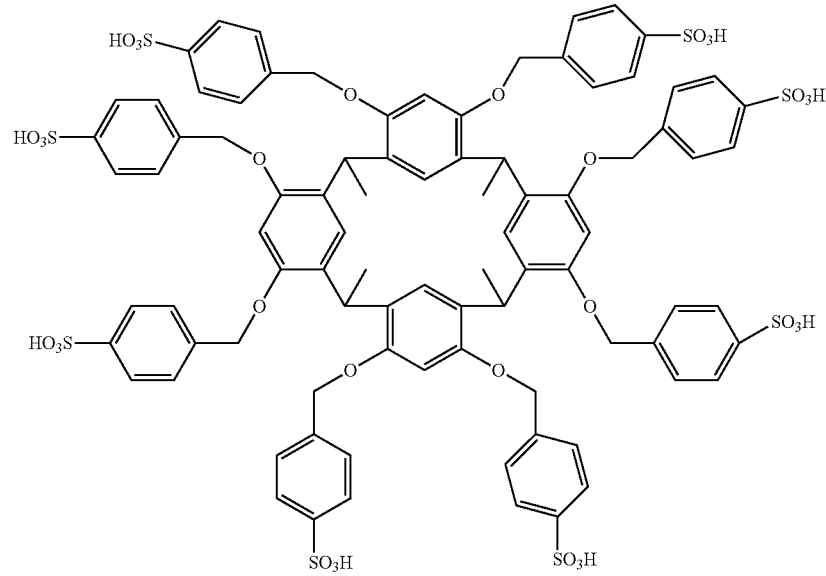
Formula 10
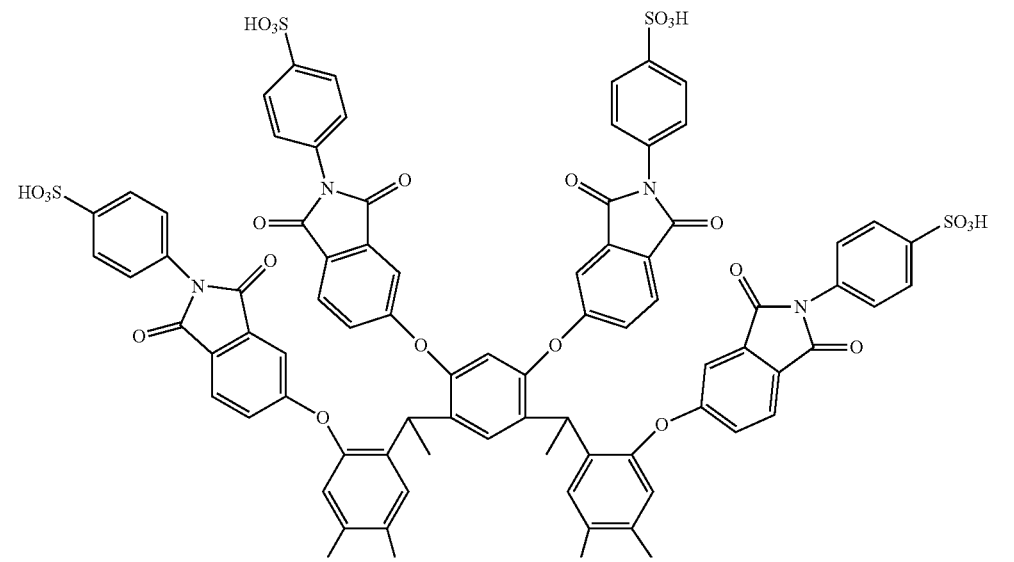
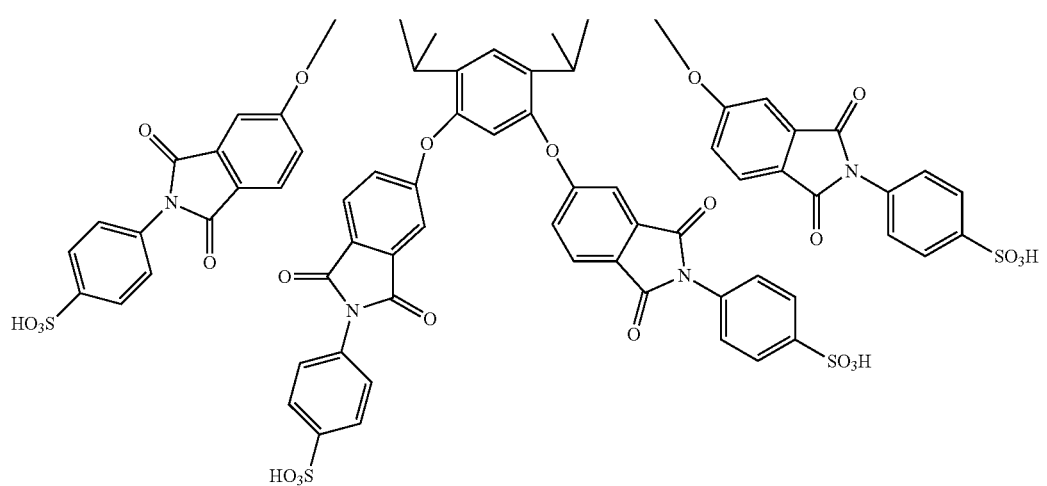

Hereinafter, a method of manufacturing the compounds represented by Formula 7, Formula 8, and Formula 10 will now be described.

Referring to Reaction Scheme 1, the synthesis of the compound in Formula 7 is as follows:

Reaction Scheme 1

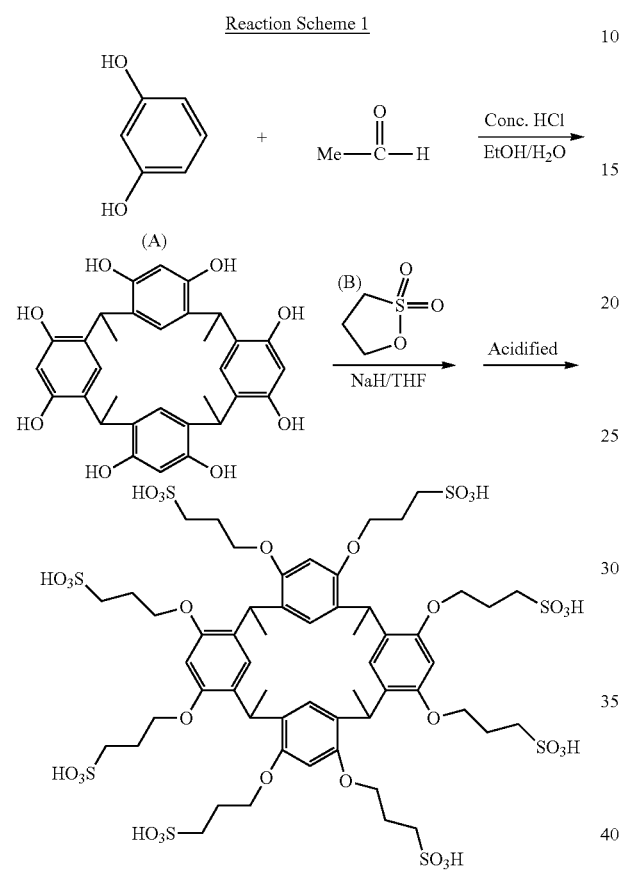

A calix[4]resorcinarene is obtained by reacting a compound (A) with acetaldehyde.

Then, the calix[4]resorcinarene is reacted with sodium hydride and a compound (B), and the resultant is acidified to obtain the compound represented by Formula 7.

The compound represented by Formula 8 is synthesized according to Reaction Schemes 1 and 2.

Referring to Reaction Scheme 2, a compound (C) is mixed with thionyl chloride and refluxed to obtain a corresponding acyl halides compound (D).

The compound (D) is mixed with $AlCl_3$ and benzene to obtain a compound (E) after Friedel-Crafts acylation.

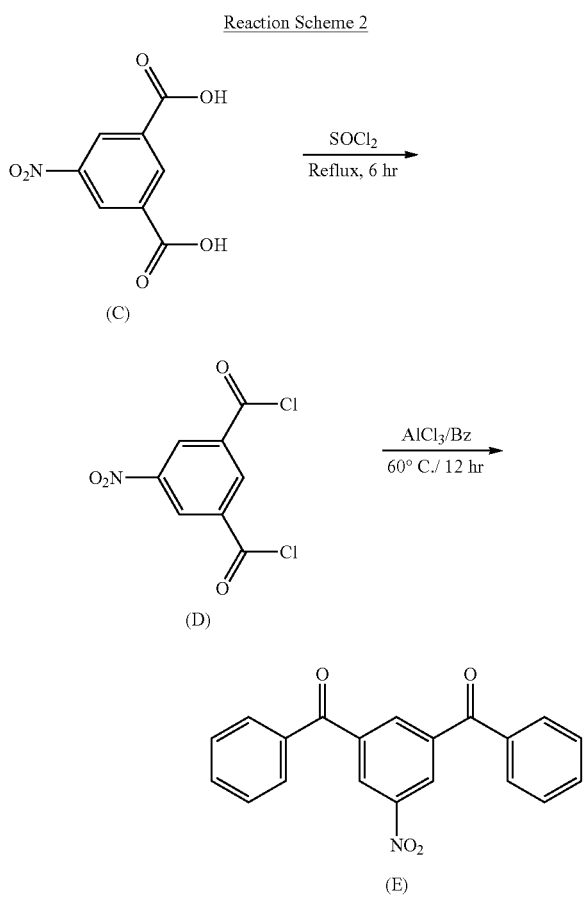

Referring to Reaction Scheme 3, the compound (E) is mixed with calix[4]resorcinarene, and the result is highly condensed in the presence of potassium carbonate to obtain a compound (F). A synthesis process of the calix[4]resorcinarene will be described later.

Reaction Scheme 3

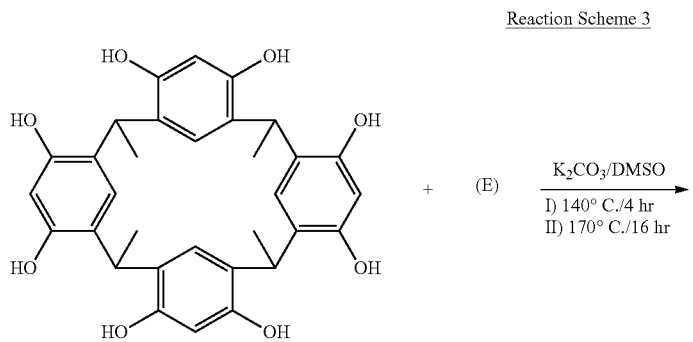

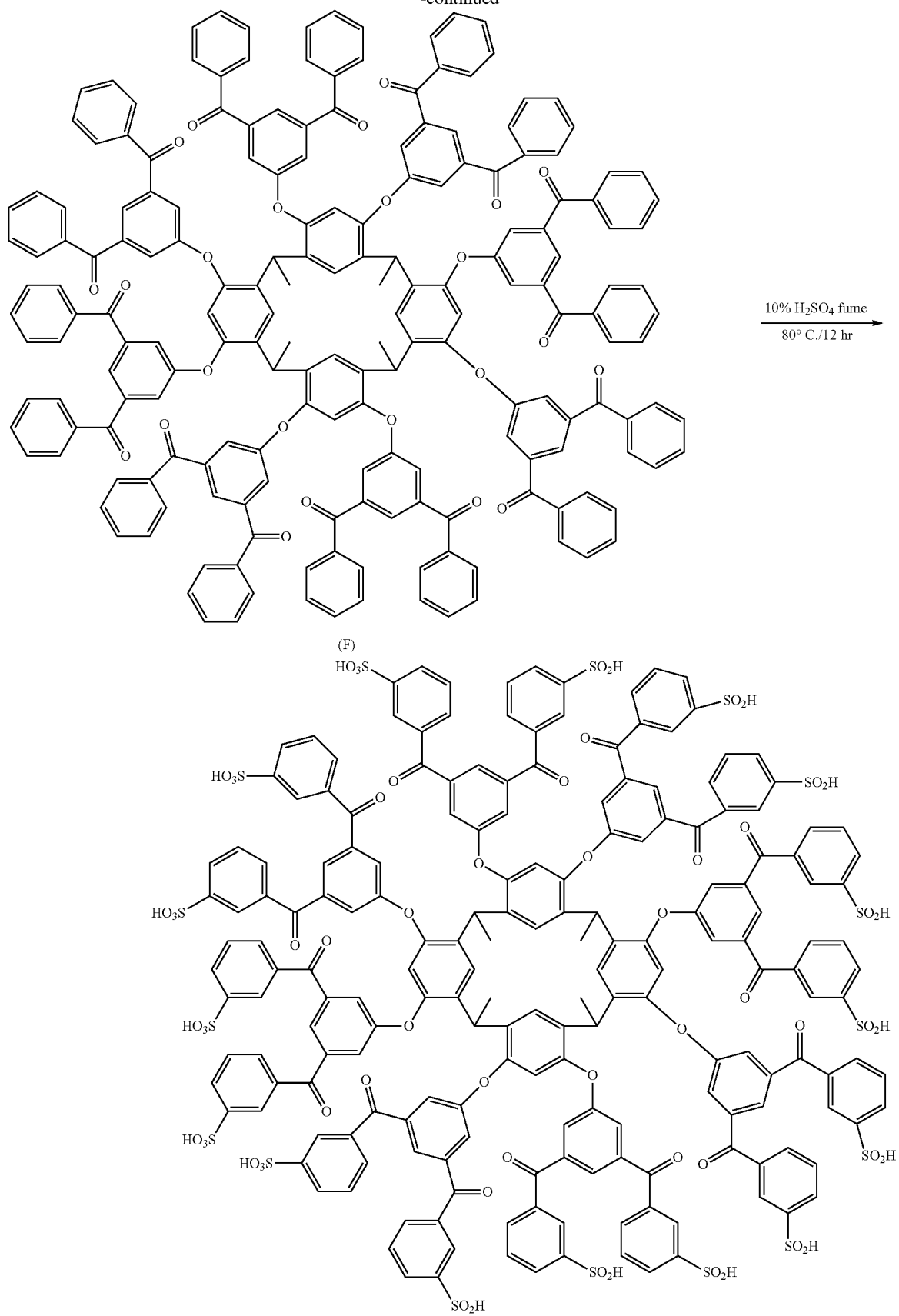
(F)

In an embodiment, the amount of the compound (E) is 1-8 moles based on 1 mole of the calix[4]resorcinarene compound.

In one embodiment, the above reaction may be performed at 140-220° C. for 1-36 hours in the presence of metallic base salts such as potassium carbonate ($K_2CO_3$), and a reaction solvent may be a polar solvent such as dimethylsulfoxide (DMSO), tetramethylene sulfone, 1-methyl-2-pyrrolidinone (NMP), N,N-dimethylformamide (DMF), or N,N-dimethylacetamide (DMAc). Also, in the initial stage of the reaction, azeotropic dehydration agents such as benzene, toluene, or xylene may be mixed and allowed to react at 120-160° C. for 2-6 hours to transform a phenol monomer into a phenoxide salt.

A sulfonation reaction is performed on the compound (F) using a strong acid such as concentrated sulfuric acid, fuming sulfuric acid, or chlorosulfonic acid to obtain the compound represented by Formula 8.

Referring to Reaction Scheme 4, a process of manufacturing the compound of Formula 10 is as follows.

Reaction Scheme 4

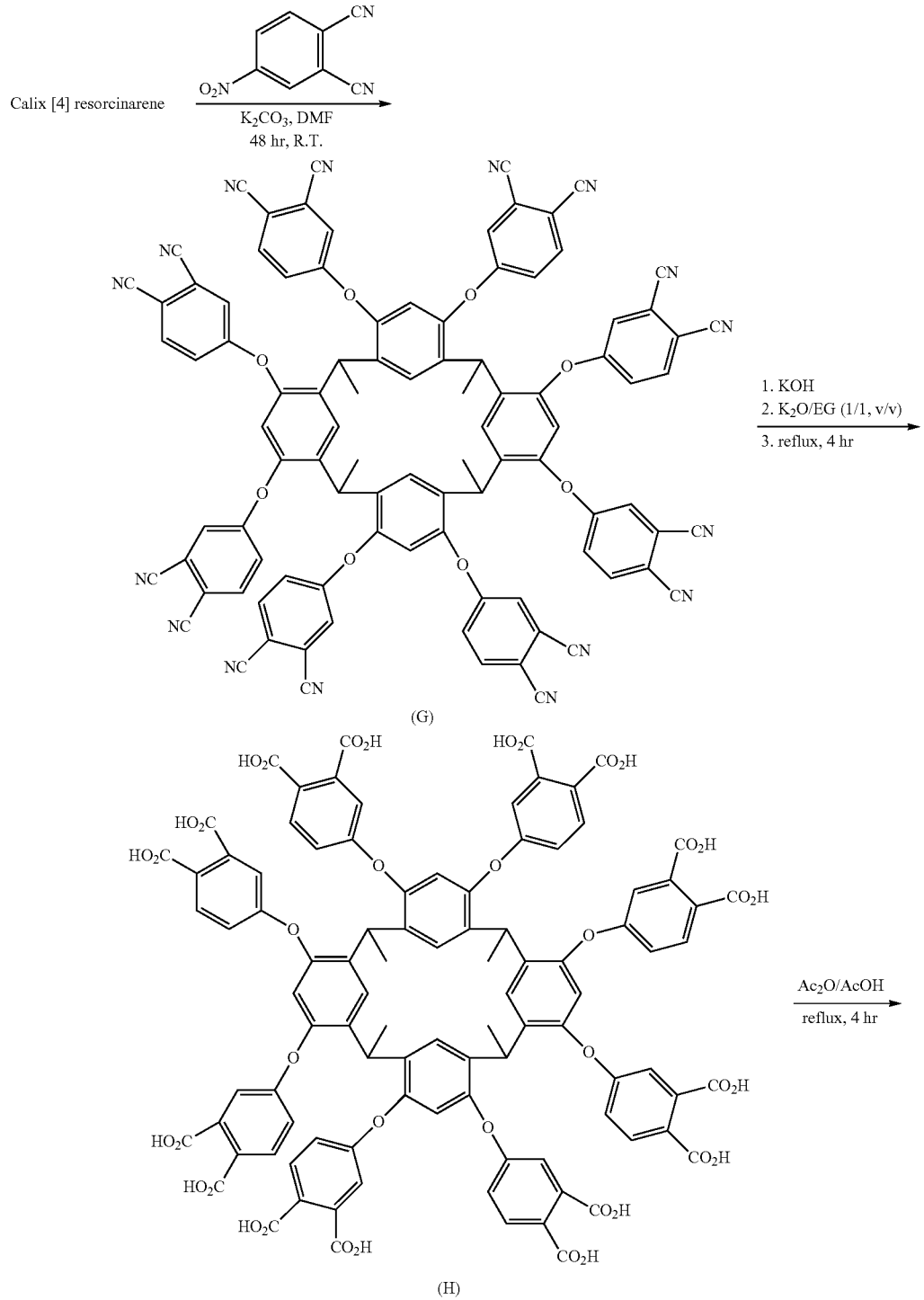

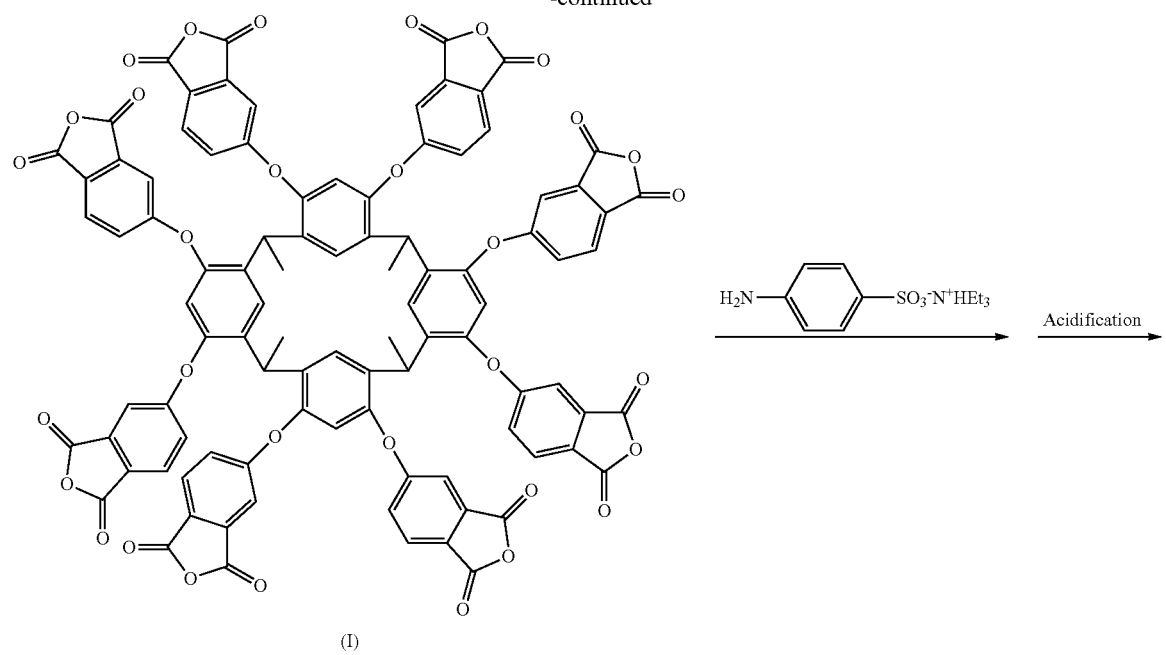
(I)
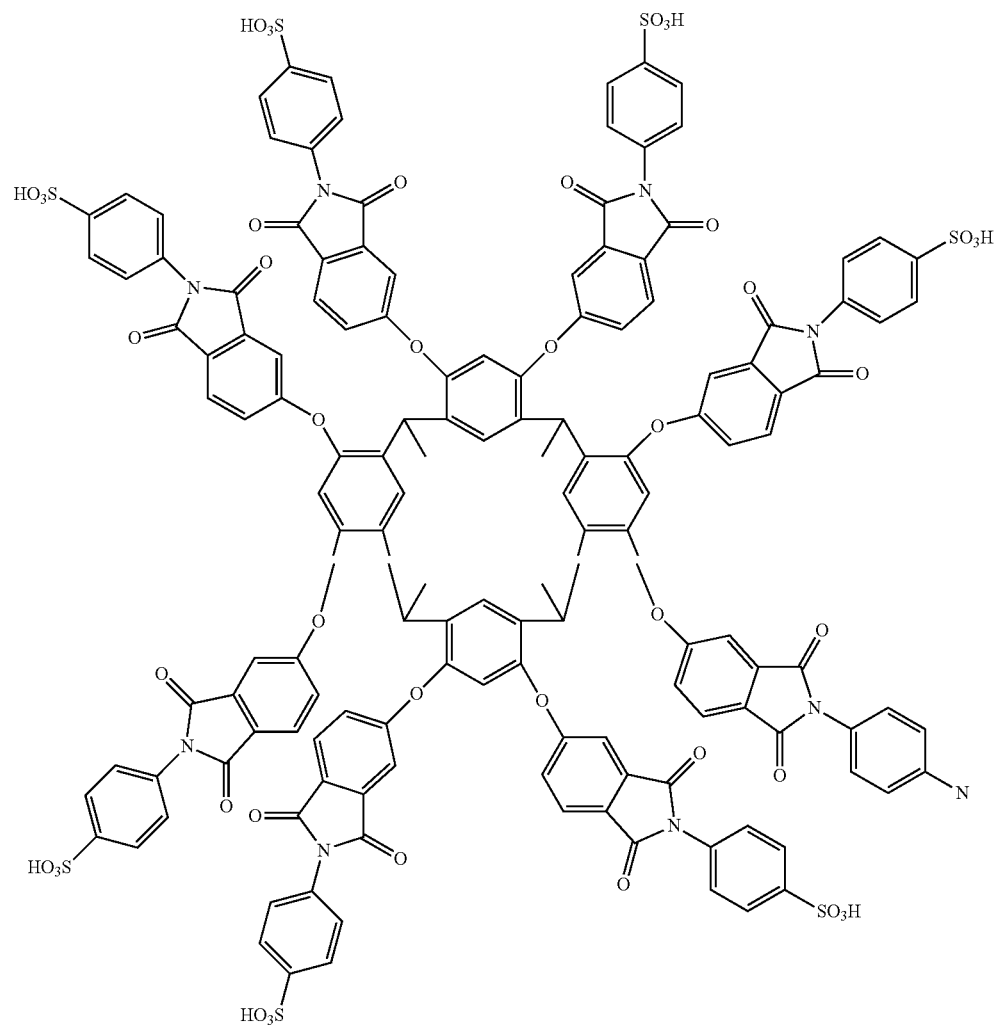

Referring to the process illustrated above, a compound (G) is obtained from the calix[4]resorcinarene by condensation at room temperature in the presence of 4-nitrophthalonitrile and potassium carbonate, and a carboxylic acid compound (H) is obtained by hydrolysis while refluxing the compound (G) with an aqueous potassium hydroxide solution. In order to induce another reaction with an $NH_2$ group, an anhydride structured compound (I) is synthesized from the carboxylic acid (the compound (H)) under an acetic acid condition. Then, the compound (I) reacts with the amino group to obtain a compound represented by Formula 10, which is the final target.

Figure 2:
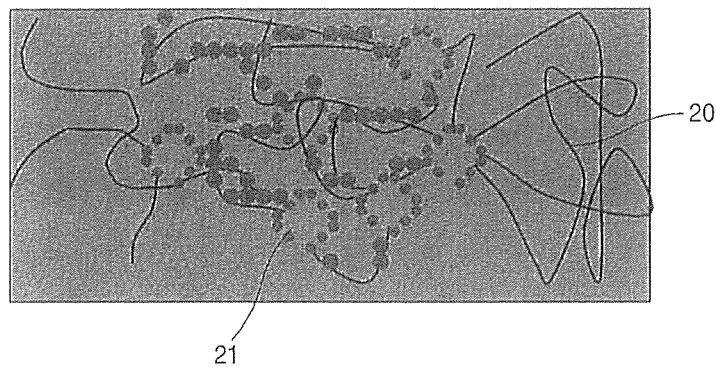
FIG. 2 is a schematic view illustrating the structure of a polymer electrolyte membrane according to an embodiment of the present invention.

Hereinafter, a polymer electrolyte membrane according to an embodiment of the present invention will be described. FIG. 2 is a schematic view illustrating the structure of a polymer electrolyte membrane of the present invention.

Referring to FIG. 2, the polymer electrolyte membrane includes a polymer matrix 20 and a solid acid 21 dispersed uniformly in the polymer matrix 20.

The polymer matrix 20 has a firm and compact structure having a hydrophobic backbone structure, and contains at least one compound selected from the group consisting of $-SO_3H$, $-COOH$, $-OH$, and $-OPO(OH)_2$ at the terminal of a side chain, and is thus hydrophilic to a certain extent, which enables it to hold the dispersed solid acid 21. The polymer matrix 20 suppresses a swelling phenomenon that occurs due to water and methanol crossover, thus maintaining excellent thermal and mechanical properties.

In one embodiment, the polymer matrix includes at least one material selected from the group consisting of sulfonated poly(ether ether ketone) (SPEEK), sulfonated poly(ether ether sulfone) (SPEES), sulfonated polyimide (SPI), polyimide, polybenzimidazole, polyether sulfone, poly(ether ether ketone), and combinations thereof. According to an embodiment of the present invention, SPEEK and SPI are used.

The SPEEK is represented by Formula 11 and SPI is represented by Formula 12.

Formula 11

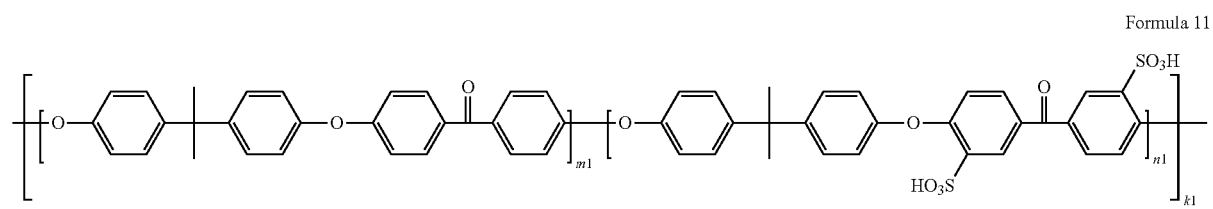

where, m1 is 0.1-0.9, n1 is 0.1-0.9, and k1 is an integer in the range of 3-1000.

If m1 is less than 0.1, swelling and permeability by a fuel such as water or alcohol increases, and if m1 is greater than 0.9, hydrogen ion conductivity is too low, even when a solid acid is added.

Formula 12

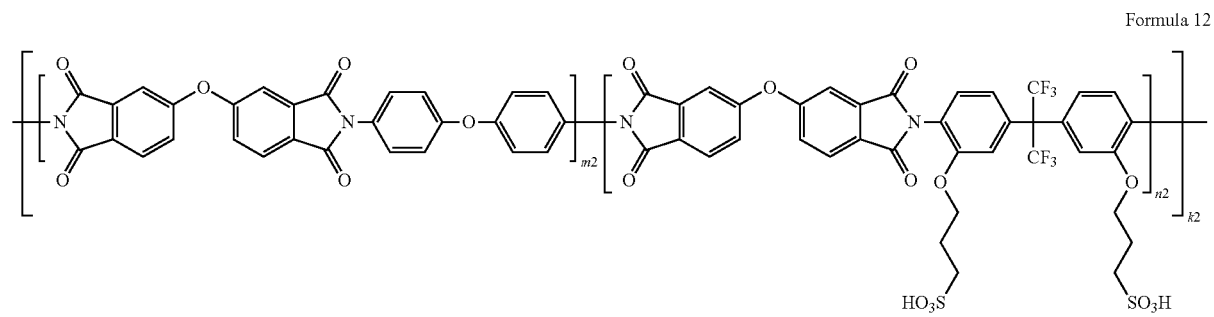

where, m2 is 0.2-0.8, n2 is 0.2-0.8, and k2 is an integer in the range of 3-1000.

Reaction Schemes 5 and 6 illustrate synthesis processes of the SPEEK in Formula 11 and the SPI in Formula 12.

Reaction Scheme 5

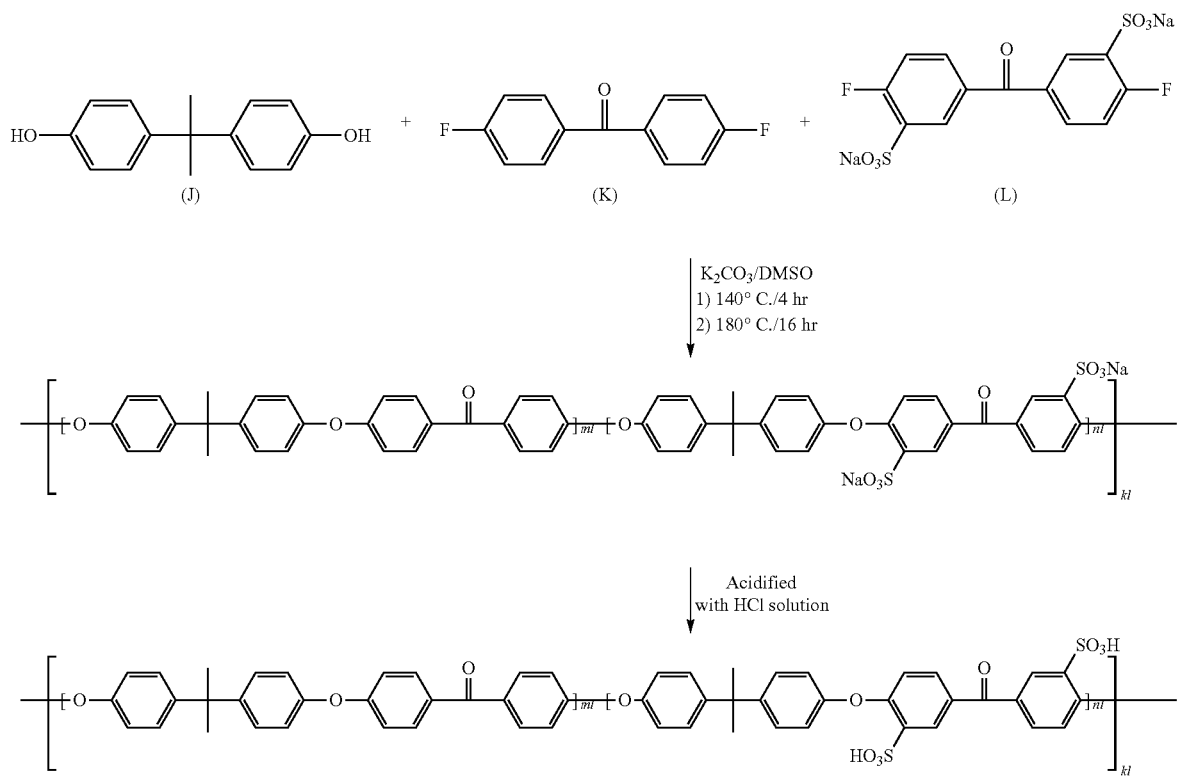

Referring to Reaction Scheme 5, a diol monomer (J), a dihalogen monomer (K) and a sulfonated dihalogen monomer (L) are mixed with a solvent and a base, and the result is polymerized to obtain a copolymer (M) having two kinds of repeating units.

In an embodiment, the polymerization may be performed at 140-220° C. for 1-36 hours in the presence of metallic base salts including base materials such as $K_2CO_3$. The polymerization solvent may be a polar solvent such as dimethylsulfoxide (DMSO), tetramethylene sulfone, 1-methyl-2-pyrrolidinone (NMP), N,N-dimethylformamide (DMF), or N,N-dimethylacetamide (DMAc). Also, in the initial stage of the reaction, azeotropic dehydration agents such as benzene, toluene, and xylene may be mixed and allowed to react at 120-160° C. for 2-6 hours to transform a phenol monomer into a phenoxide salt.

In an embodiment, the amount of the dihalogen monomer (K) is 0.1-0.9 moles based on 1 mole of the diol monomer (J) and the amount of the sulfonated dihalogen monomer (L) is 0.1-0.9 moles based on 1 mole of the diol monomer (J).

The copolymer (M) is acidified in an acid solution to obtain the SPEEK of Formula 11.

Reaction Scheme 6

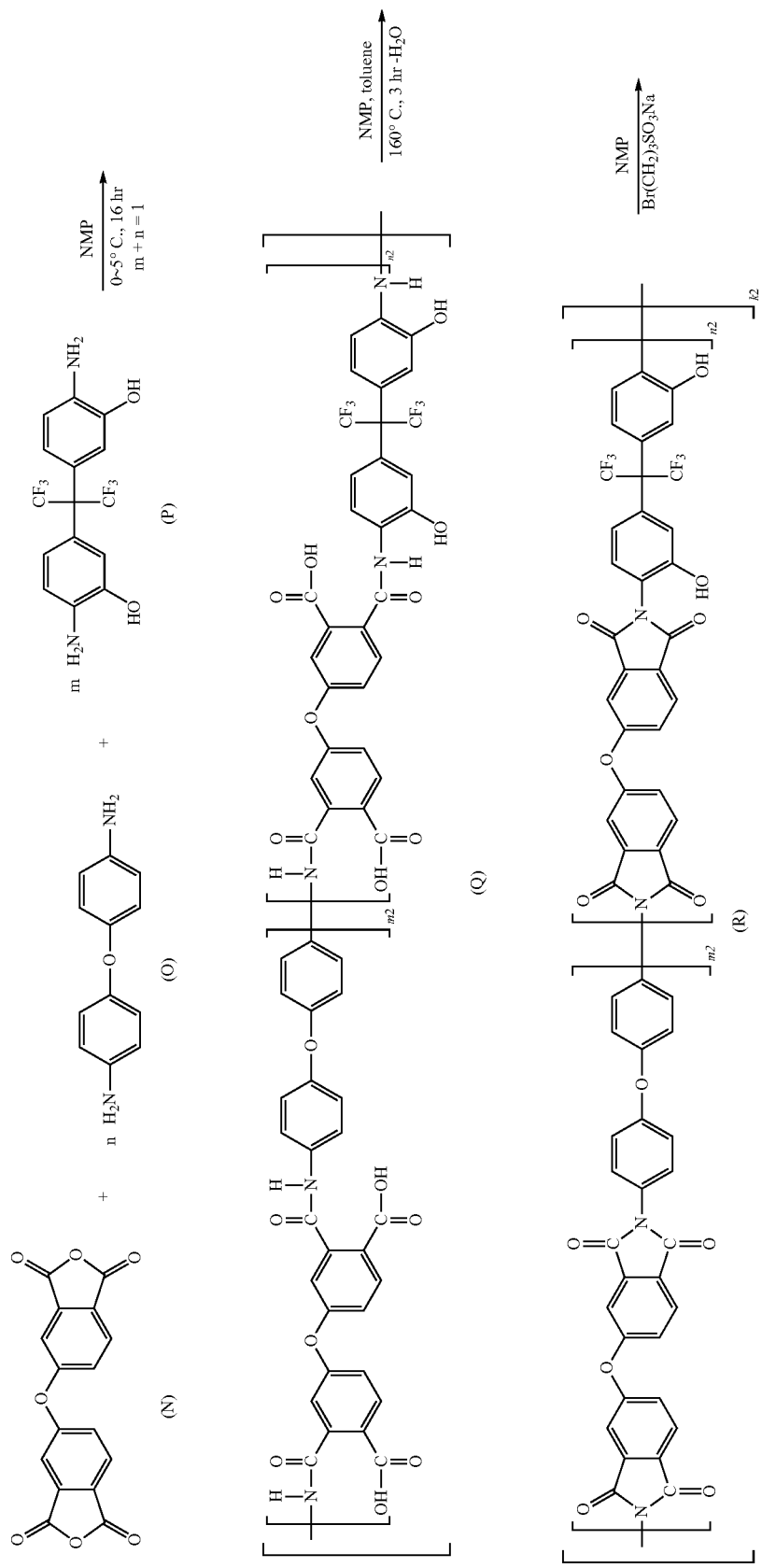

-continued
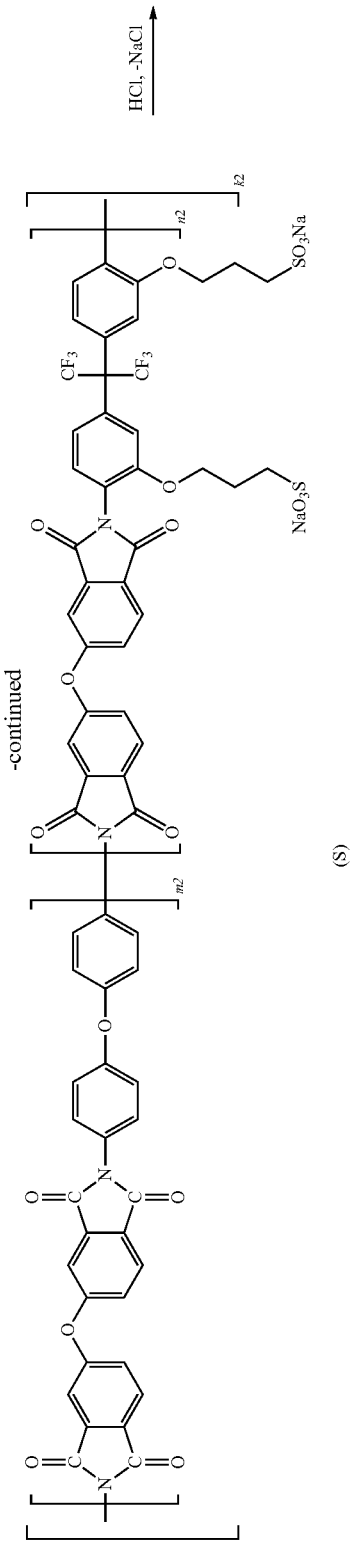
$\xrightarrow{\text{HCl, -NaCl}}$
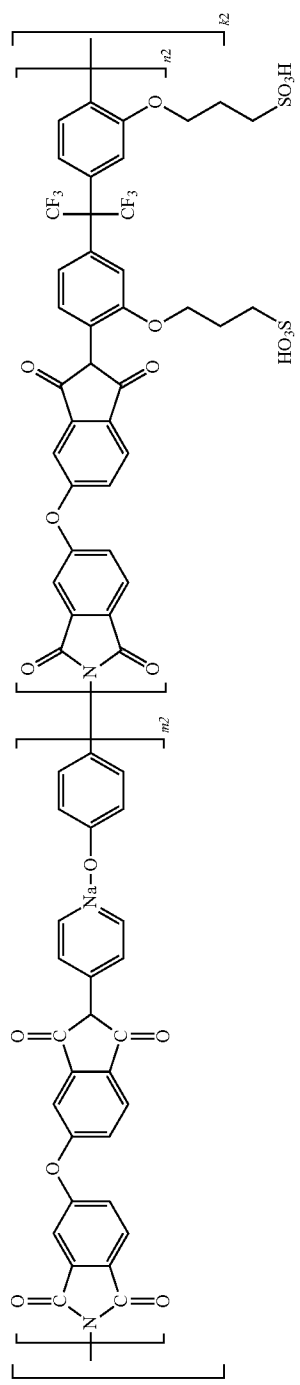
(S)

Referring to Reaction Scheme 6, an acid anhydride monomer (N), a monomer (O) having a diamino group, and a monomer (P) having a hydroxyl group and a diamino group are first mixed and polymerized to obtain polyamide acid (O) having 2 different kinds of repeating units. In an embodiment, the amount of the monomer (O) having a diamino group may be 0.2-0.8 moles based on 1 mole of the acid anhydride monomer (N) and the amount of the monomer (P) having a hydroxyl group and a diamino group may be 0.2-0.8 moles based on 1 mole of the acid anhydride monomer (N).

In an embodiment, the polymerization is performed at −10-50° C., for example, 0-5° C. The polymerization time can vary according to temperature, and may be 12-36 hours, for example, 16 hours.

The polyamide acid (Q) is heat treated to obtain a corresponding polyimide (R) and a compound (S) is obtained by substituting a hydroxyl group of the polyimide with a propyloxy group having a sulfonate group at a terminal. Then, the compound (S) is reacted with oxygen to obtain the SPI of Formula 12.

The polymer electrolyte membrane of one embodiment can have ionic conductivity since the solid acid according to an embodiment of the present invention is uniformly dispersed in the polymer matrix as described above. That is, an acidic functional group attached to the terminal of the side chain of the polymer matrix and an acidic functional group existing on a surface of a dendrimer solid acid work together to provide high ionic conductivity.

Conventionally, a large amount of an ionic conductivity terminal group such as a sulfonic acid group attaches to the polymer used for the conventional polymer electrolyte membrane, thereby causing swelling. However, in the polymer matrix according to an embodiment of the present invention, a minimum amount of an ionic conductivity terminal group for ionic conduction is attached, thereby avoiding swelling which occurs due to moisture.

Hereinafter, a membrane and electrode assembly (MEA) including the polymer electrolyte membrane will be described.

The present invention provides a MEA comprising a cathode having a catalyst layer and a diffusion layer, an anode having a catalyst layer and a diffusion layer, and an electrolyte membrane interposed between the cathode and the anode, wherein the electrolyte membrane includes the polymer electrolyte membrane according to an embodiment of the present invention.

The cathode and anode both having a catalyst layer and a diffusion layer are well known in the field of fuel cells. Also, the electrolyte membrane includes the polymer electrolyte membrane according to an embodiment of the present invention. The polymer electrolyte membrane can be used independently in the electrolyte membrane or can be combined with other membranes having ionic conductivity.

Hereinafter, a fuel cell including the polymer electrolyte membrane according to an embodiment of the present invention will be described.

The present invention provides a fuel cell comprising a cathode having a catalyst layer and a diffusion layer, an anode having a catalyst layer and a diffusion layer, and an electrolyte membrane interposed between the cathode and the anode, wherein the electrolyte membrane includes the polymer electrolyte membrane according to an embodiment of the present invention.

The cathode and anode both having a catalyst layer and a diffusion layer are well known in the field of fuel cells. Also, the electrolyte membrane includes the polymer electrolyte membrane according to an embodiment of the present invention. The polymer electrolyte membrane can be used independently in the electrolyte membrane or can be combined with other membranes having ionic conductivity.

The fuel cell can use any conventional operating process, and thus, a detailed description thereof is omitted herein.

The present invention will now be described with the following examples. The following examples are for illustrative purposes only, and are not intended to limit the scope of the invention.

Synthesis Example 1

Preparing a Compound in Formula 7

Figure 3:
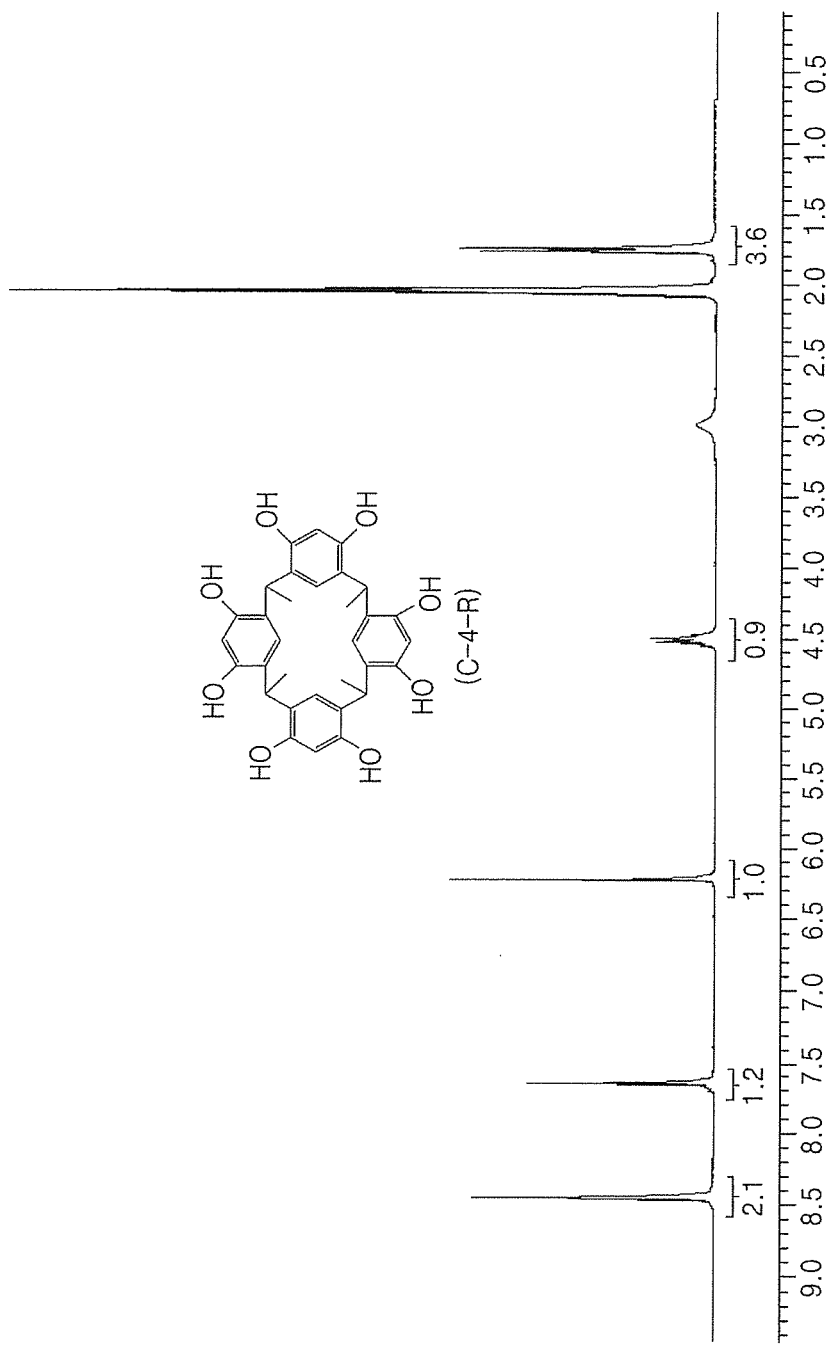
FIG. 3 is a Nuclear Magnetic Resonance (NMR) analysis spectrum of calix[4]resorcinarene.

33.03 g (0.3 mol) of resorcinol (compound A) and 13.22 g (16.8 ml, 0.3 mol) of acetaldehyde were dissolved in 300 ml of a 50 vol % aqueous ethanol solution and the result was heated to 75° C. 75 ml of concentrated hydrochloric acid was slowly added to the resulting mixture and the reaction was maintained at 75° C. for 1 hour. The resultant mixture was cooled with ice water and a precipitate was filtered through a glass filter. The filtered solution was evaporated and then the precipitate was separated again. The precipitate was recrystallized using a 50 vol % aqueous ethanol solution to obtain 30.11 g of a calix[4]resorcinarene compound (yield: 74.1%). The structure of the calix[4]resorcinarene compound was identified through Nuclear Magnetic Resonance (NMR) analysis, the results of which are illustrated in FIG. 3.

3.0 g (5.5 mmol) of the calix[4]resorcinarene compound was dissolved in 60 ml of anhydrous THF, and then 1.164 g (48.5 mmol) of sodium hydride (NaH) was added under nitrogen. After a reaction occurred for 1 hour at room temperature, 5.92 g (48.47 mmol) of 1,3-propane sultone (compound B) was slowly added in an ice-bath, and the result was refluxed for 24 hours. The mixture was cooled to room temperature and a precipitate was filtered through a glass filter. Then, the result was washed with ether and dried under reduced pressure to synthesize a sodium salt type intermediate.

Figure 4:
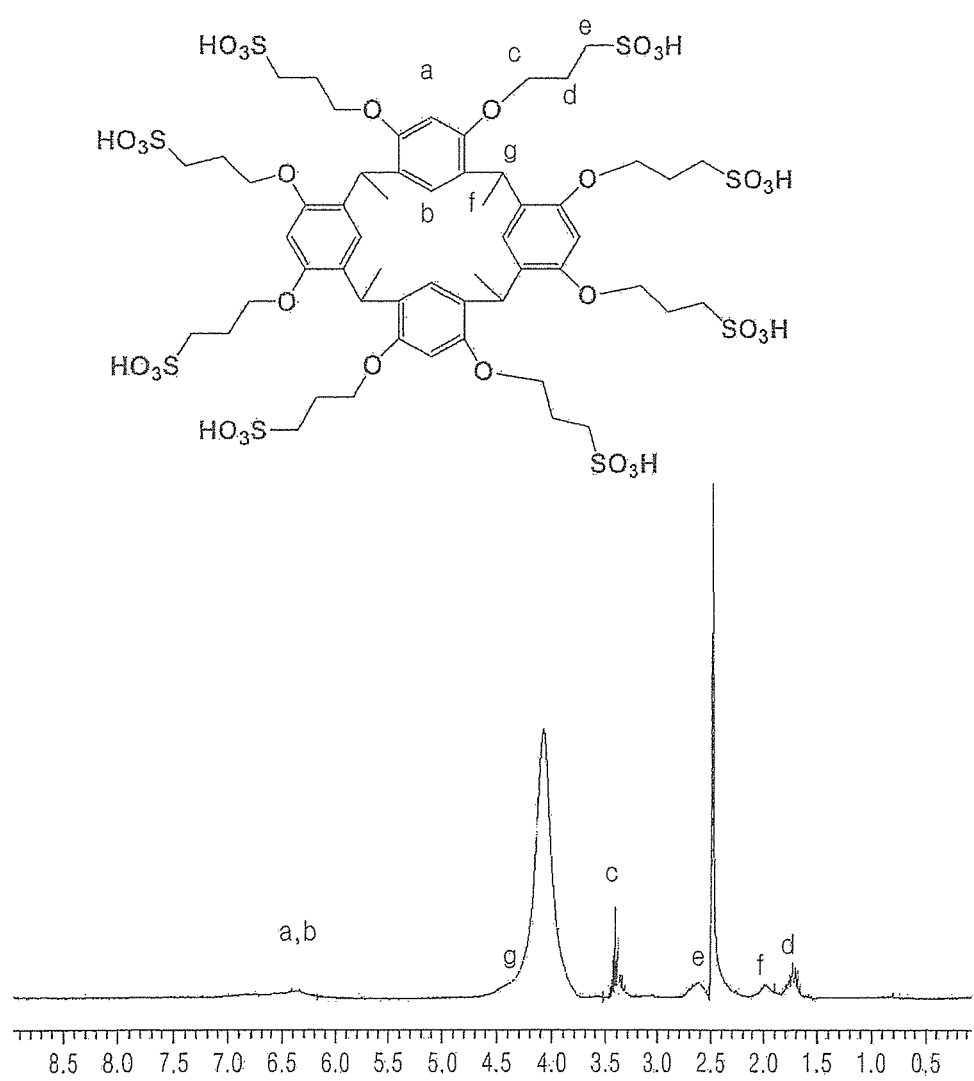
FIG. 4 is an NMR analysis spectrum of a compound represented by Formula 7 according to an embodiment of the present invention.
Figure 5:
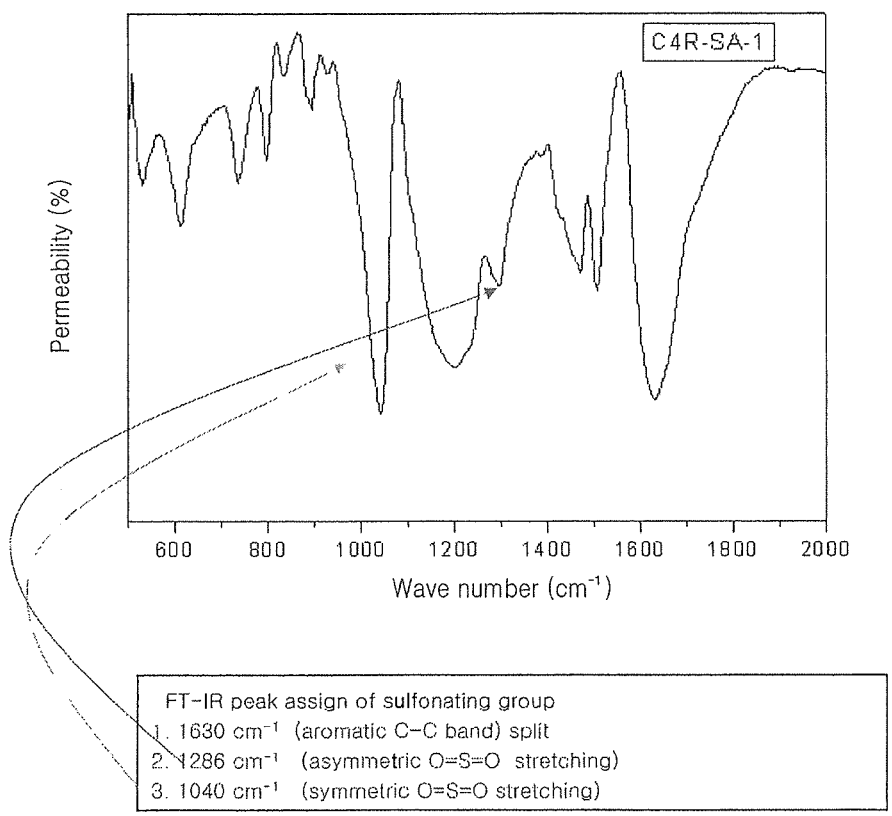
FIG. 5 is a Fourier Transform Infrared (FT-IR) spectrum of the compound represented by Formula 7 according to an embodiment of the present invention.

The intermediate was dissolved in an aqueous methanol solution and a small amount of diluted hydrochloric acid was added thereto. Then, a precursor of the solid acid was transformed into the solid acid, and the produced salts were filtered and removed. A solvent was removed under reduced pressure, and 6.37 g (yield: 76%) of a light yellow precipitate was obtained. The structure of Formula 7 was identified through NMR analysis, as illustrated in FIG. 4, and a sulfonate group was identified through Fourier Transform Infrared Spectroscopy (FT-IR), the results of which are illustrated in FIG. 5.

Synthesis Example 2

Preparing a Compound in Formula 8

Under a nitrogen atmosphere, 20 g (94.7 mmol) of 5-Nitroisophthalic acid (compound C) was dissolved in 100 ml of thionyl chloride to which 5 drops of pyridine were added, and the result was stirred at room temperature for 2 hours, and was refluxed for 6 hours. Then, excessive thionyl chloride was removed under reduced pressure to obtain a yellow mixture, and the result was cooled with ice water. Anhydrous hexane was added to the yellow mixture to obtain a white precipitate, and the white precipitate was filtered and dried under reduced pressure to obtain 22.3 g (yield: 95%) of 2-Nitroterephthaloyl chloride (D), a white solid compound.

Figure 6:
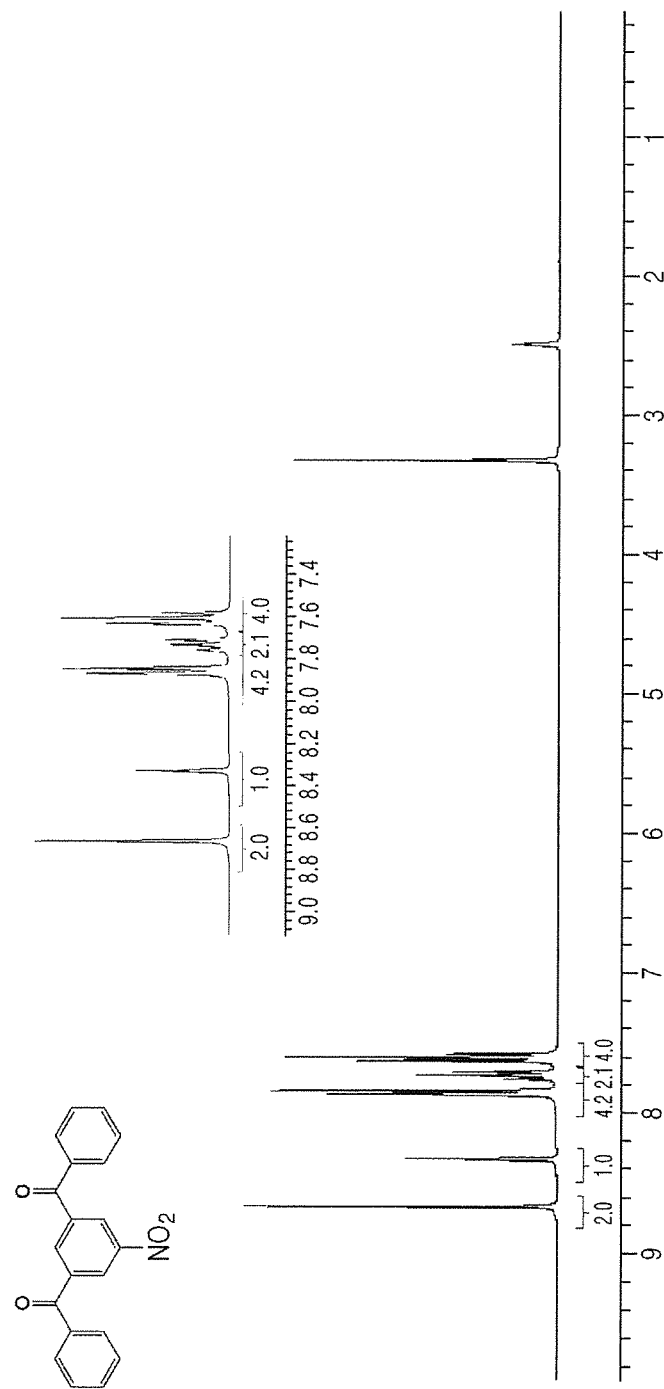
FIG. 6 is an NMR analysis spectrum of a compound (E) obtained according to an Example of the present invention.

16.0 g (0.064 mol) of 2-Nitroterephthaloyl chloride (D) was dissolved in 140 ml of anhydrous benzene and 25.9 g (0.194 mol) of anhydrous $AlCl_3$ was added thereto under a nitrogen atmosphere. The result was left to sit at room temperature for 1 hour. Then, the result was stirred for 1 hour and then left to react at 60° C. for 12 hours. The product was cooled to room temperature and added to a 5% aqueous hydrochloric acid solution to decompose an $AlCl_3$ complex. An organic layer was washed with a $NaHCO_3$ solution extracted using dichloromethane and water, and dried using $MgSO_4$. A solvent was distilled for removal, and the result was recrystallized with ethanol to obtain 17.3 g (yield: 81%) of a yellow crystalline solid compound (E). The structure of the yellow crystalline solid compound (E) was identified through NMR analysis, the results of which are illustrated in FIG. 6.

Figure 7:
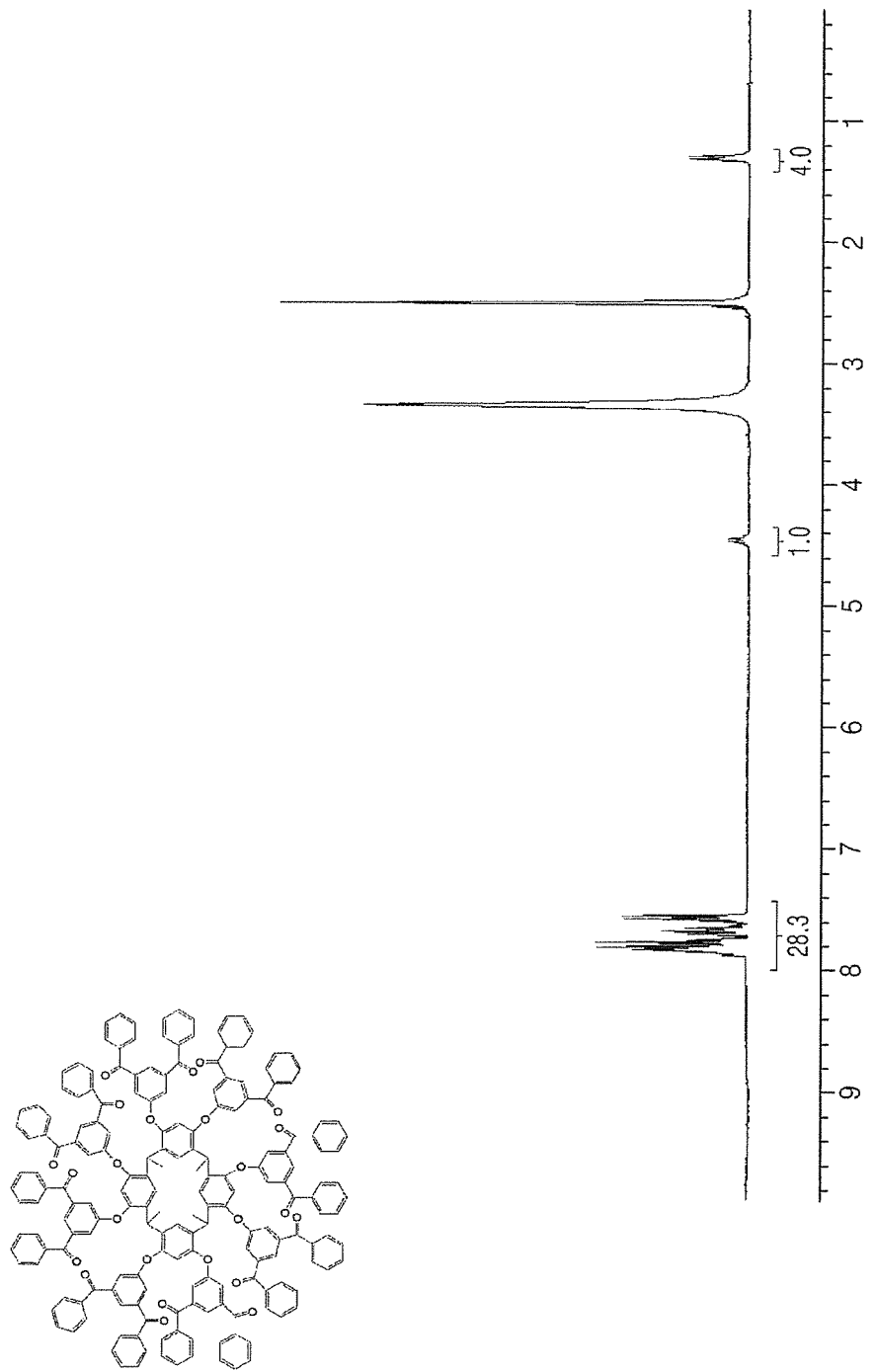
FIG. 7 is an NMR analysis spectrum of a compound (F) obtained according to an Example of the present invention.

3.0 g (5.50 mmol) of the calix[4]resorcinarene compound prepared according to Synthesis Example 1, 14.75 g (44.5 mmol) of the compound (E), and 6.09 g of anhydrous $K_2CO_3$ were put in a flask in which a Dean-Stark trap was installed, and 90 ml of dimethylsulfoxide (DMSO) and 50 ml of toluene were mixed as a solvent and added to the flask. The mixture was refluxed at 140° C. for 4 hours under a nitrogen atmosphere to remove generated water, and toluene was removed. The temperature was raised to 170° C. to allow a reaction to occur for 16 hours. After cooling to room temperature, the product was precipitated in methanol and the precipitated solid was washed with hot water to remove inorganic materials. The washed solid compound was dried under reduced pressure to obtain 14.6 g (yield: 94%) of a solid compound (F). The structure of the solid compound (F) was identified through NMR analysis, the results of which are illustrated in FIG. 7.

4.0 g (1.419 mmol) of the compound (F) (solid acid precursor) was completely dissolved in 20 ml of fuming sulfuric acid ($SO_3$, 60%) at room temperature, and allowed to react at 80° C. for 12 hours. The product was cooled to room temperature, and then a precipitate was formed in ether. The precipitate was filtered and dissolved in water, filtered through a dialysis membrane and refined to prepare the compound of Formula 8.

Figure 8:
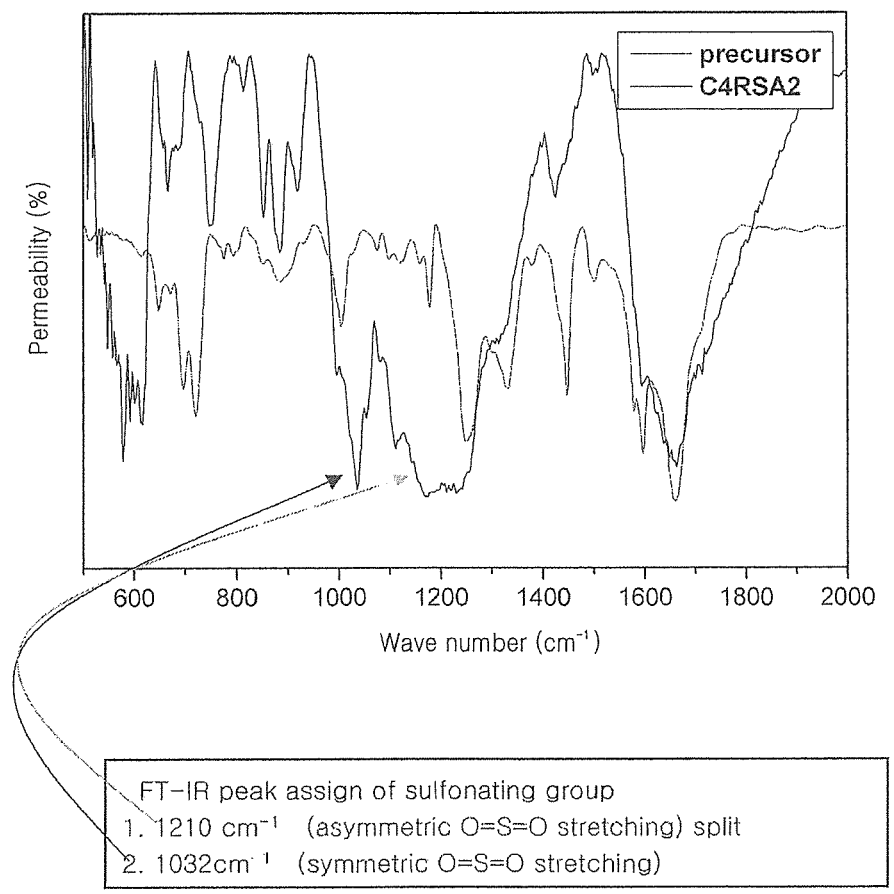
FIG. 8 is an FT-IR spectrum of a compound represented by Formula 8 according to an embodiment of the present invention.

The compound of Formula 8 was identified through FT-IR analysis, the results of which are illustrated in FIG. 8.

Synthesis Example 3

Preparing Sulfonated Poly(Ether Ether Ketone) 1 (SPEEK1) (m1=0.8, n1=0.2, and Mn=Approx. 50,000) in Formula 11

10.812 g (47.36 mmol) of the compound (J), 8.267 g (37.88 mmol) of the compound (K), and 4.0 g (9.47 mmol) of the compound (L) and 8.5 g of anhydrous $K_2CO_3$ were put in a 250 mL, 3-neck round flask in which a Dean-Stark trap was installed, and 120 ml of dimethylsulfoxide (DMSO) and 60 ml of toluene were mixed as a solvent and added to the flask.

The mixture was refluxed at 140° C. for 4 hours under a nitrogen atmosphere to remove generated water, and toluene was removed. The temperature was raised to 180° C. to perform polymerization for 16 hours. After cooling to room temperature, the product was precipitated in methanol, and the precipitated copolymer was washed with hot water 3 times to remove inorganic materials. The formed copolymer was dried at 100° C. for 24 hours.

The copolymer (sodium salt type) was dissolved in dimethylsulfoxide (DMSO) and diluted hydrochloric acid was added to react for 24 hours. The mixture of methanol and water was added to the mixed solution to obtain precipitate and thus, a conductive copolymer substituted for a hydrogen ion was prepared.

Synthesis Example 4

Preparing Sulfonated Poly(Ether Ether Ketone) 2 (SPEEK2) (m1=0.66, n1=0.33) in Formula 11

A conductive copolymer was prepared according to Synthesis Example 3, except that 3.242 g (14.20 mmol) of the compound (J), 2.066 g (9.47 mmol) of the compound (K), 1.997 g (4.73 mmol) of the compound (L), 1.96 g of anhydrous $K_2CO_3$, 36 ml of DMSO, and 20 ml of toluene were used.

Examples 1 through 7

Preparing Polymer Electrolyte Membrane

According to the details shown in Table 1, one of the SPEEK1 obtained according to Synthesis Example 3 and the SPEEK2 obtained according to Synthesis Example 4, and one of the compounds of Formula 7 and Formula 8 were completely dissolved in dimethylsulfoxide (DMSO) and cast. Then, the result was dried in an oven at 80° C. for 24 hours to prepare a polymer electrolyte membrane, and the polymer electrolyte membrane was immersed in distilled water for 24 hours.

The thickness, ionic conductivity and methanol permeability of each of the polymer electrolyte membranes prepared according to the above process were measured, and the results are shown in Table 2.

Examples 8 Through 9

In order to prepare a NAFION™ electrolyte membrane, a NAFION™ solution (manufactured by Dupont) was cast, dried in an oven at 60° C. for 24 hours, and dried under a reduced pressure at 120° C. to prepare a polymer membrane. The electrolyte membrane and one of the compounds of Formula 7 and Formula 8, according to the details in Table 1, were completely dissolved in dimethylsulfoxide (DMSO), cast, and dried in an oven at 80° C. for 24 hours to prepare a polymer electrolyte membrane.

Then, the membrane was immersed in a 1.0 M aqueous hydrochloric acid solution for 24 hours to allow protonation, and then immersed in distilled water for 24 hours.

The thickness, ionic conductivity and methanol permeability of each of the polymer electrolyte membranes prepared according to the above process were measured, and the results are shown in Table 2.

Examples 10 Through 13

According to the details in Table 1, the polymer of Formula 12, an SPI prepared according to Reaction Scheme 6 with the ratio of m2 to n2 being 5:5, and one compound selected from Formula 7 and Formula 8 were completely dissolved in 1-methyl-2-pyrrolidinone (NMP) and coated using a spin coating method to cast at 110° C. for 12 hours, to prepare a polymer electrolyte membrane.

The thickness, ionic conductivity and methanol permeability of each of the polymer electrolyte membranes prepared according to the above process were measured, and the results are shown in Table 2.

Comparative Example 1

A polymer electrolyte membrane was prepared according to Example 1 except that a solid acid of Formula 7 or 8 was not used.

Comparative Example 2

A polymer electrolyte membrane was prepared according to Example 6 except that a solid acid of Formula 7 or 8 was not used.

Comparative Example 3

A polymer electrolyte membrane was prepared according to Example 8 except that a solid acid of Formula 7 or 8 was not used.

Comparative Example 4

A polymer electrolyte membrane was prepared according to Example 10 except that a solid acid of Formula 7 or 8 was not used.

The thickness, ionic conductivity and methanol permeability of each of the polymer electrolyte membranes prepared according to comparative examples 1 through 4 were measured, and the results are shown in Table 2.

TABLE 1

| | Polymer | | Solid acid | |
|---|---|---|---|---|
| | Type | Amount (parts by weight) | Type | Amount (parts by weight) |
| Comparative Example1 | SPEEK1 | 100 | — | — |
| Example1 | SPEEK1 | 97.5 | compound in Formula 7 | 2.5 |
| Example2 | SPEEK1 | 95 | compound in Formula 7 | 5 |
| Example3 | SPEEK1 | 90 | compound in Formula 7 | 10 |
| Example4 | SPEEK1 | 95 | compound in Formula 8 | 5 |
| Example5 | SPEEK1 | 90 | compound in Formula 8 | 10 |
| Comparative Example2 | SPEEK2 | 100 | — | — |
| Example6 | SPEEK2 | 90 | compound in Formula 7 | 10 |
| Example7 | SPEEK2 | 90 | compound in Formula 8 | 10 |
| Comparative Example3 | NAFION | 100 | — | — |
| Example8 | NAFION | 95 | compound in Formula 7 | 5 |
| Example9 | NAFION | 95 | compound in Formula 8 | 5 |
| Comparative Example 4 | SPI | 100 | — | — |
| Example10 | SPI | 95 | compound in Formula 7 | 5 |
| Example11 | SPI | 90 | compound in Formula 7 | 10 |
| Example12 | SPI | 95 | compound in Formula 8 | 5 |
| Example13 | SPI | 90 | compound in Formula 8 | 10 |

TABLE 2

| | Thickness (μm) | Proton conductivity (S/cm) | Methanol permeability (cm²/sec) |
|---|---|---|---|
| Comparative Example1 | 105 | $4.67 \times 10^{-4}$ | $5.14 \times 10^{-8}$ |
| Example1 | 118 | $4.00 \times 10^{-4}$ | $6.19 \times 10^{-8}$ |
| Example2 | 129 | $3.49 \times 10^{-3}$ | $8.30 \times 10^{-8}$ |
| Example3 | 138 | $3.72 \times 10^{-3}$ | $8.50 \times 10^{-8}$ |
| Example4 | 131 | $4.98 \times 10^{-3}$ | $8.27 \times 10^{-8}$ |
| Example5 | 145 | $5.28 \times 10^{-3}$ | $8.61 \times 10^{-8}$ |
| Comparative Example2 | 100 | $2.66 \times 10^{-3}$ | $8.08 \times 10^{-8}$ |
| Example6 | 138 | $3.40 \times 10^{-3}$ | $7.23 \times 10^{-8}$ |
| Example7 | 150 | $3.98 \times 10^{-3}$ | $6.94 \times 10^{-8}$ |
| Comparative Example3 | 92 | $1.68 \times 10^{-3}$ | $1.58 \times 10^{-6}$ |
| Example8 | 118 | $6.71 \times 10^{-3}$ | $8.25 \times 10^{-7}$ |
| Example9 | 130 | $8.25 \times 10^{-3}$ | $9.41 \times 10^{-7}$ |
| Comparative Example 4 | 23 | $2.60 \times 10^{-6}$ | $2.73 \times 10^{-9}$ |
| Example10 | 41 | $8.74 \times 10^{-5}$ | $4.15 \times 10^{-8}$ |
| Example11 | 58 | $4.91 \times 10^{-4}$ | $7.43 \times 10^{-8}$ |
| Example12 | 54 | $7.93 \times 10^{-5}$ | $1.94 \times 10^{-8}$ |
| Example13 | 75 | $1.08 \times 10^{-4}$ | $3.81 \times 10^{-8}$ |

As illustrated in Table 2, the greater the amount of the solid acid which is a series of calixresorcinarenes of the present invention, the greater the ionic conductivity. Also, methanol permeability is increased but the increasing rate is slowed down gradually.

In a SPEEK having high conductivity used in the present invention, the effectiveness to methanol permeability is not effective, compared to conductivity. In NAFION™, ions and methanol move through microchannels located in an inner membrane, but if the solid acid of the present invention is added, a large amount of the solid acid exists in the microchannels, thereby improving ionic conductivity and reducing methanol permeability. Also, if the membrane is prepared by adding the solid acid of the present invention to SPI, methanol permeability is slightly higher, but ionic conductivity is increased 100 times more than that of methanol permeability. Accordingly, the solid acid of the present invention greatly improves ionic conductivity without a deleterious effect on methanol permeability.

The polymer electrolyte membrane according to the present invention contains an ion conducting compound having calixarene or calixresorcinarene at the core, in which at least one of the hydroxyl groups is substituted by an organic group having a cation exchange group at a terminal, thereby reducing methanol crossover and improving ionic conductivity. A fuel cell having improved efficiency can be obtained by using the polymer electrolyte membrane.

While the present invention has been described with reference to exemplary embodiments thereof, it will be understood by those of ordinary skill in the art that various changes in form and details may be made therein without departing from the spirit and scope of the present invention as defined by the following claims.

What is claimed is:

1. A polymer electrolyte membrane comprising:
   a polymer matrix; and
   a solid acid having a core of calixarene or calixresorcinarene, wherein the solid acid is an ion conducting compound in which at least one of the hydroxyl groups is substituted by an organic group having a cation exchange group at a terminal end.

2. The polymer electrolyte membrane of claim 1, wherein the polymer matrix includes at least one material selected from the group consisting of sulfonated poly(ether ether ketone) (SPEEK), sulfonated poly(ether ether sulfone) (SPEES), sulfonated polyimide (SPI), polyimide, polybenzimidazole, polyethersulfone, and poly(ether ether ketone).

3. The polymer electrolyte membrane of claim 2, wherein the SPEEK is represented by Formula 11 and the SPI is represented by Formula 12:

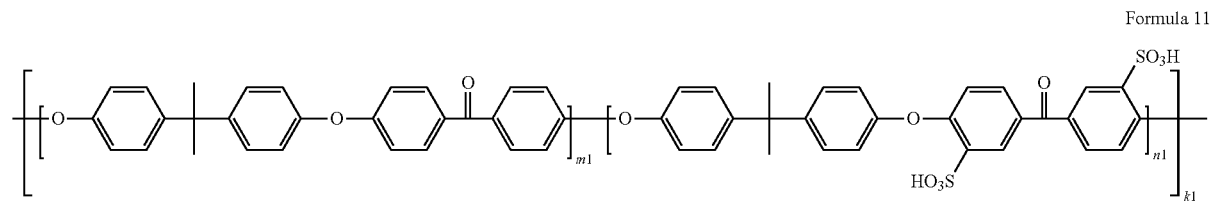

Formula 11 where m1 is from 0.1-0.9, n1 is from 0.1-0.9, and k1 is an integer in the range of 3-1000;

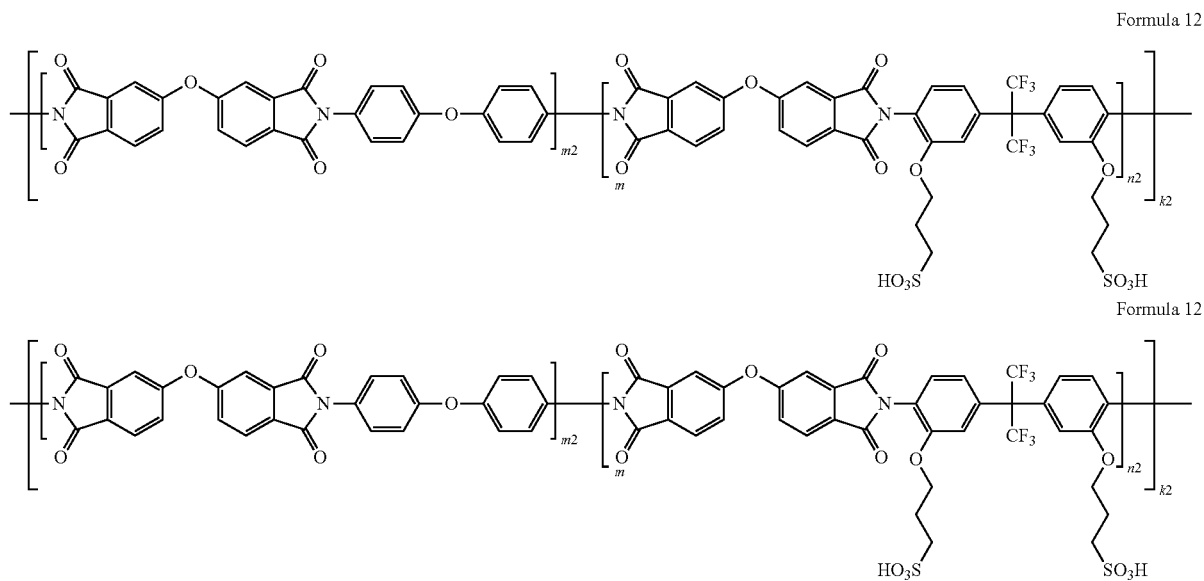

Formula 12

Formula 12 where m2 is from 0.2-0.8, n2 is from 0.2-0.8, and k2 is an integer in the range of 3-1000.

4. The polymer electrolyte membrane of claim 1, wherein the amount of the solid acid is in the range of 0.1-40 parts by weight based on 100 parts by weight of the polymer matrix.

5. A fuel cell comprising:
a cathode;
an anode; and
the polymer electrolyte membrane of claim 1 interposed between the cathode and the anode.

* * * * *